United States Patent
Yazaki et al.

(10) Patent No.: US 6,858,625 B1
(45) Date of Patent: Feb. 22, 2005

(54) QUINOLINECARBOXYLIC ACID DERIVATIVE OR SALTS THEREOF

(75) Inventors: Akira Yazaki, Takata-gun (JP); Yoshiko Niino, Takata-gun (JP); Yasuhiro Kuramoto, Takata-gun (JP); Yuzo Hirao, Takata-gun (JP); Yoshihiro Ohshita, Takata-gun (JP); Norihiro Hayashi, Takata-gun (JP); Hirotaka Amano, Takata-gun (JP)

(73) Assignee: Wakunaga Pharmaceutical Co., Ltd., Osaka (JP)

( * ) Notice: Subject to any disclaimer, the term of this patent is extended or adjusted under 35 U.S.C. 154(b) by 175 days.

(21) Appl. No.: 10/019,436

(22) PCT Filed: Jun. 22, 2000

(86) PCT No.: PCT/JP00/04096

§ 371 (c)(1),
(2), (4) Date: Dec. 31, 2001

(87) PCT Pub. No.: WO01/02390

PCT Pub. Date: Jan. 11, 2001

(30) Foreign Application Priority Data

Jul. 1, 1999 (JP) ............................................. 11/187492

(51) Int. Cl.⁷ .................. A61K 31/4709; C07D 401/14
(52) U.S. Cl. ....................................... 514/312; 546/156
(58) Field of Search ........................... 514/312; 546/156

(56) References Cited

U.S. PATENT DOCUMENTS 5,998,436 A * 12/1999 Yazaki et al. ................ 514/312

FOREIGN PATENT DOCUMENTS

| EP | 0 388 298 | 9/1990 |
| EP | 0 897 919 | 2/1999 |
| EP | 0 911 327 | 4/1999 |
| EP | 0 945 435 | 9/1999 |
| JP | 11-292873 | 10/1999 |
| WO | WO 95/05373 | 2/1995 |
| WO | 97/11068 | 3/1997 |

* cited by examiner

*Primary Examiner*—Patricia L. Morris
(74) *Attorney, Agent, or Firm*—Oblon, Spivak, McClelland, Maier & Neustadt, P.C.

(57) ABSTRACT

This invention relates to 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid or a salt thereof, and also to a medicine containing the same. This compound has characteristic features that, when administered orally, it has extremely high blood half-life and bioavailability while retaining properties that it has extremely high antimicrobial effects and has low toxicity. It can be used widely as preventives, therapeutics and the like for various infectious diseases of human and animals.

10 Claims, 3 Drawing Sheets

QUINOLINECARBOXYLIC ACID DERIVATIVE OR SALTS THEREOF

TECHNICAL FIELD

Figure 1:
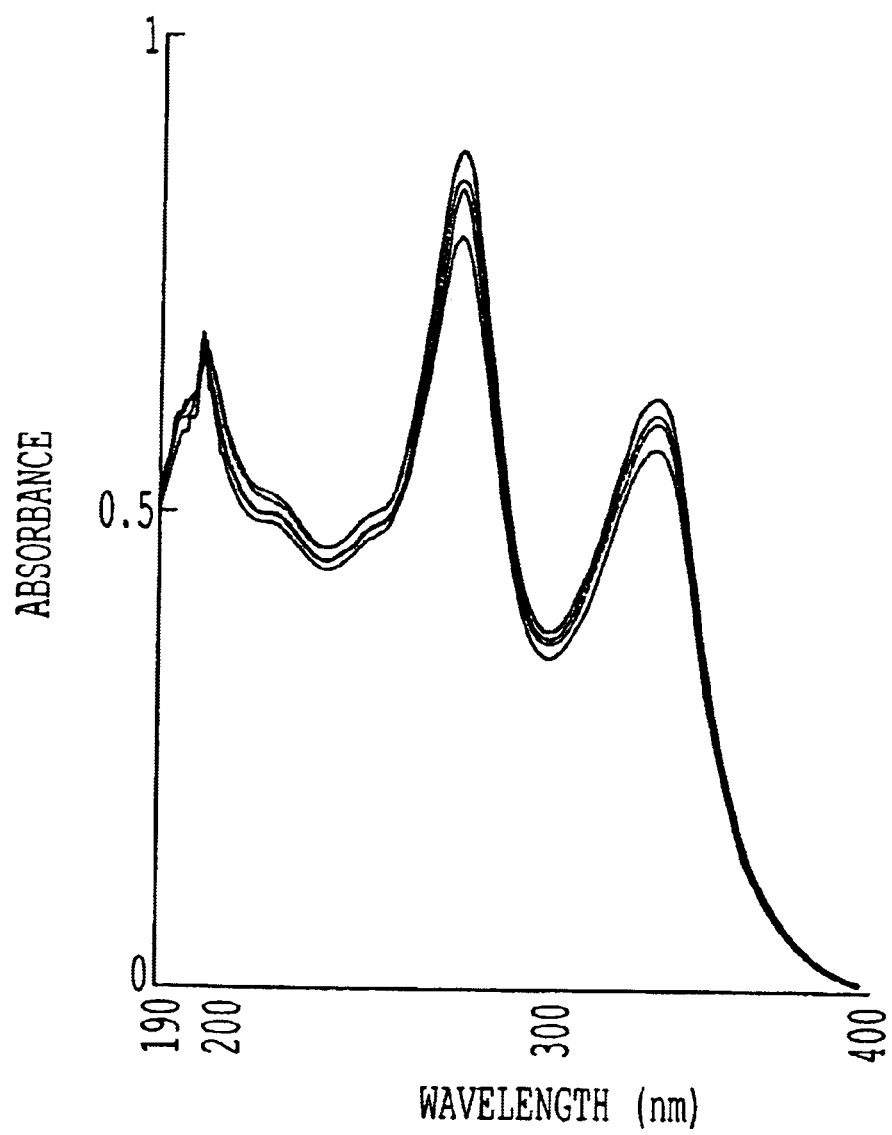
Figure 2:
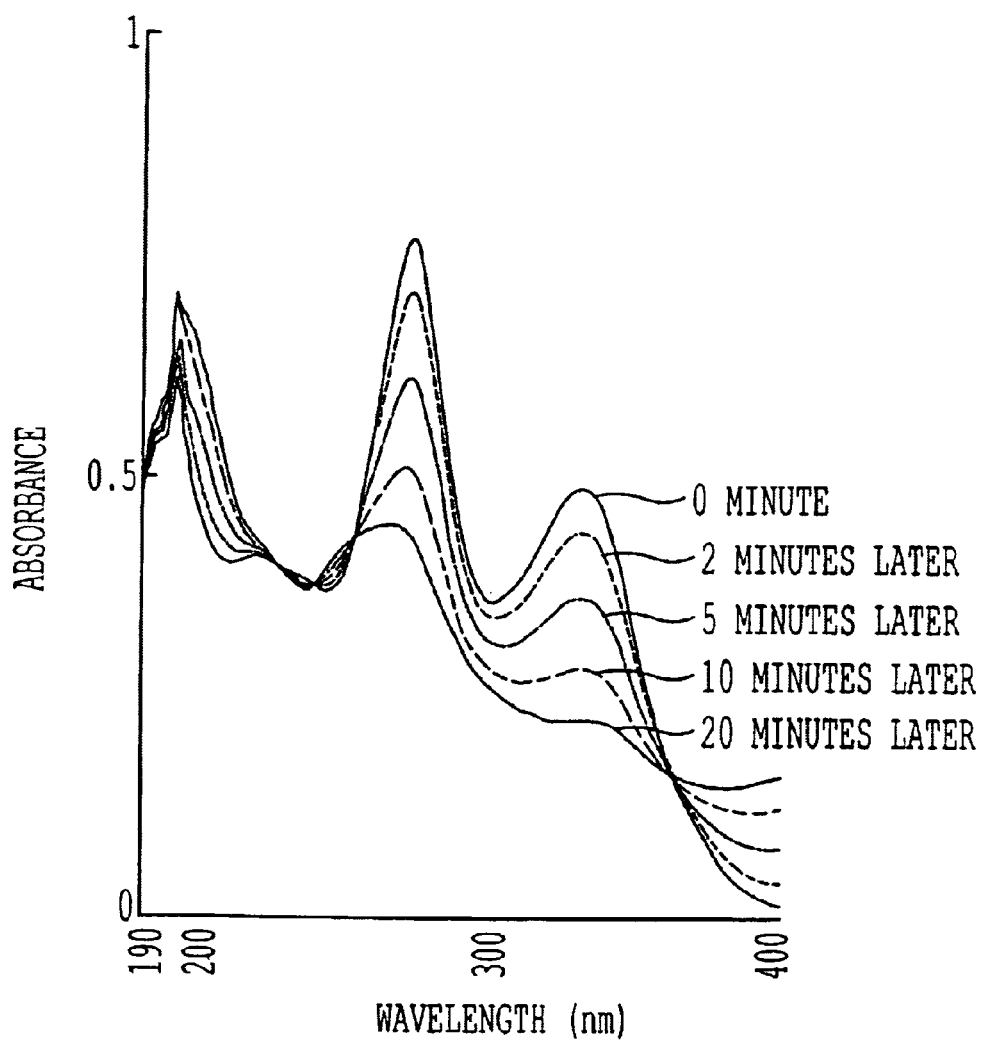
Figure 3:
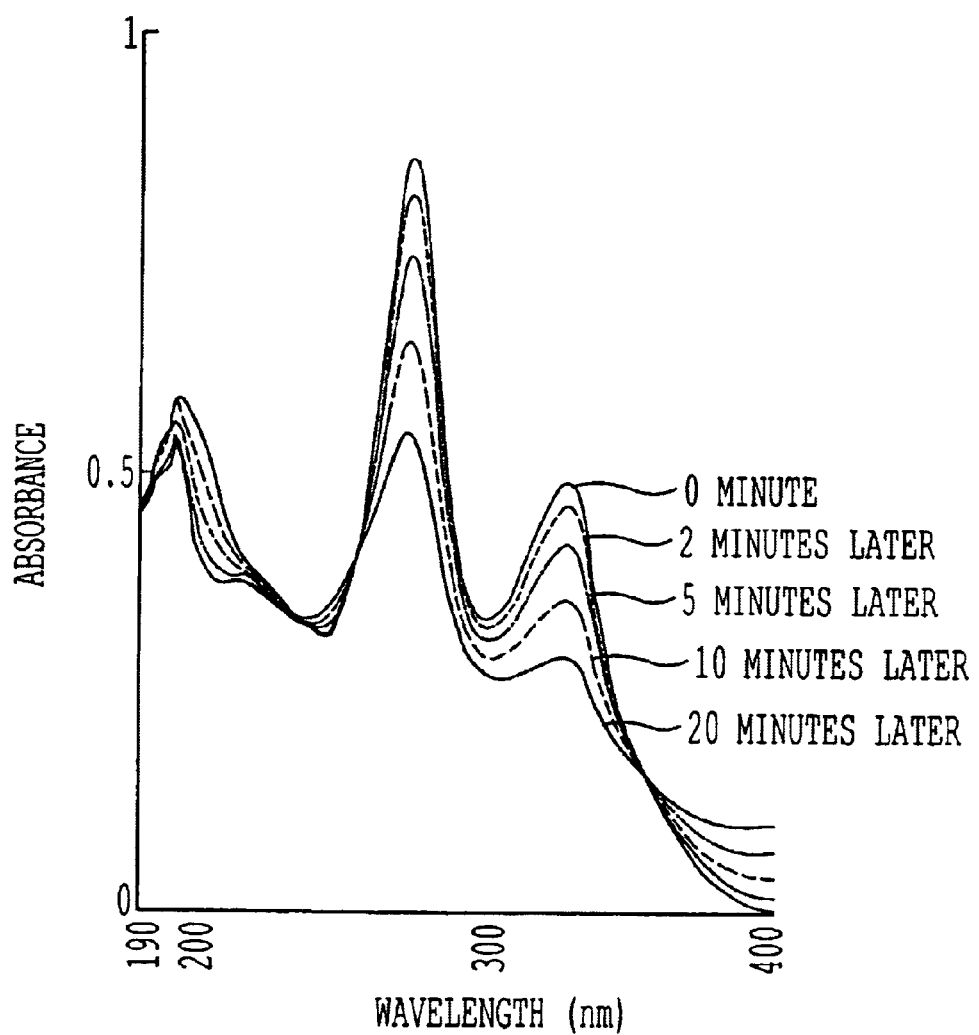

This invention relates to a quinolinecarboxylic acid derivative and salts thereof, which have excellent antimicrobial effects and oral absorption, and also to antimicrobial agents comprising the same.

BACKGROUND ART

Compounds having the basic skeleton of quinolinecarboxylic acid are known to include many compounds useful as synthetic antimicrobials for their excellent antimicrobial activities and broad antimicrobial spectra. Among such compounds, norfloxacin (JP 53-141286 A), enoxacin (JP 55-31042 A), ofloxacin (JP 57-46986 A), ciprofloxacin (JP 58-74667 A), tosufloxacin (JP 60-228479) and the like are widely used in clinical practice as therapeutic agents for infectious diseases.

These compounds, however, are not sufficient yet in antimicrobial activities, intestinal absorption and metabolic stability, and still involve many problems to be solved, such as reductions of phototoxicity and cytotoxicity both of which are specific to quinolinecarboxylic acid and its derivatives. Recently, the emergence of resistant bacteria to these medicaments has also raised a problem.

DISCLOSURE OF THE INVENTION

An object of the present invention is, therefore, to provide an antimicrobial agent, which is clinically applicable, has excellent antimicrobial potency, intestinal absorption and metabolic stability, and has low side effects.

Under the foregoing circumstances, the present inventors conducted extensive research to provide clinically excellent medicinal agents. As a result, it was found that pyridonecarboxylic acid derivatives—which are each represented by the following formula (I):

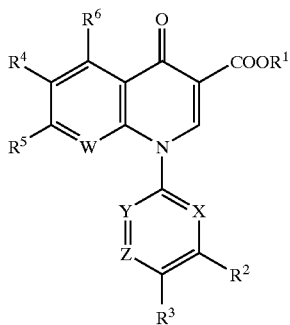

(I)

wherein $R^1$ represents a hydrogen atom or a carboxyl-protecting group, $R^2$ represents a hydroxyl group, a lower alkoxy group or a substituted or unsubstituted amino group, $R^3$ represents a hydrogen atom or a halogen atom, $R^4$ represents a hydrogen atom or a halogen atom, $R^5$ represents a halogen atom or a substituted or unsubstituted, saturated cyclic amino group, $R^6$ represents a hydrogen atom, a halogen atom, a nitro group or a protected or unprotected amino group, X, Y and Z maybe the same or different and each independently represents a nitrogen atom, —CH= or —CR$^7$= in which $R^7$ represents a lower alkyl group, a halogen atom or a cyano group with a proviso that at least one of X, Y and Z represents a nitrogen atom, and W represents a nitrogen atom or —CR$^8$= in which $R^8$ represents a hydrogen atom, a halogen atom or a lower alkyl group—and salts thereof have excellent antimicrobial potency and are useful as synthetic antimicrobial agents, and a PCT international application was filed on them (WO 97/11068 A).

The present inventors have proceeded with further research. As a result, it has been found that among the above-described pyridonecarboxylic acid derivatives (I), 1-(6-amino-3,5-difluoropyridin-2-yl)-8-bromo-7-(3-ethylamino-azetidin-1-yl)-6-fluoro-4-oxo-1,4-dihydroquinoline-3-carboxylic acid—which has a 6-amino-3,5-difluoropyridinyl group at the 1-position, an ethylaminoazetidinyl group at the 7-position, and a bromine atom at the 8-position, and represented by the following formula:

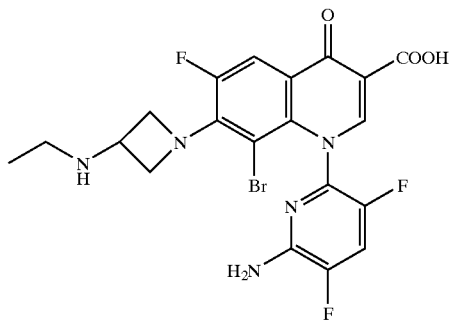

and its salts have excellent properties that they have extremely good antimicrobial potency and broad antimicrobial spectrum covering resistant bacteria, do not show phototoxicity which is toxicity specific to quinolone and are lower in antihypertensive effect and side effects to skin, such as eruption, than known compounds of similar structures, and moreover, are long in blood half-life, extremely high in bioavailability, and extremely useful as preventives and therapeutics for various infectious diseases, leading to the completion of the present invention.

Described specifically, the present invention provides 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid (hereinafter called "Compound 1") or a salt thereof.

The present invention also provides a medicine comprising as an active ingredient Compound 1 or a salt thereof.

The present invention also provides a medicinal composition comprising Compound 1 or a salt thereof and a pharmaceutically acceptable carrier.

The present invention further provides use of Compound 1 or a salt thereof as a medicine.

The present invention still further provides a method for the treatment of an infectious disease, which comprises administering Compound 1 or a salt thereof.

BEST MODES FOR CARRYING OUT THE INVENTION

Compound 1 of the present invention can be formed into both acid addition salts and base addition salts. It is to be noted that those forming chelates with boron compounds are also included in such salts.

Examples of the acid addition salts can include (a) salts with mineral acids such as hydrochloric acid, sulfuric acid and phosphoric acid, (b) salts with organic carboxylic acids such as formic acid, acetic acid, citric acid, trichloroacetic acid, trifluoroacetic acid, fumaric acid and maleic acid, and (c) salts with sulfonic acids such as methanesulfonic acid, benzenesulfonic acid, p-toluenesulfonic acid, mesitylene-sulfonic acid and naphthalenesulfonic acid, while examples of the base addition salts can include (a') salts with alkali metals such as sodium and potassium, (b') salts with alkaline earth metals such as calcium and magnesium, (c') the ammonium salt, (d') salts with nitrogen-containing organic bases such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine and N,N'-dibenzyl-ethylenediamine. Illustrative of the boron compounds are boron halides such as boron fluoride, and lower acyloxyborons such as acetoxyboron. Of these, acid addition salts are preferred, with the maleate, the methanesulfonate, the p-toluenesulfonate and the hydrochloride being particularly preferred.

Compound 1 or the salt thereof according to the present invention can exists not only in the non-solvated form but also in the form of the hydrate or a solvate. Accordingly, the compounds according to the present invention each embrace its all crystalline forms, its hydrate, and its solvates.

Compound 1 or the salt according to the present invention can each be produced by a desired process. An exemplary process can be illustrated as follows:

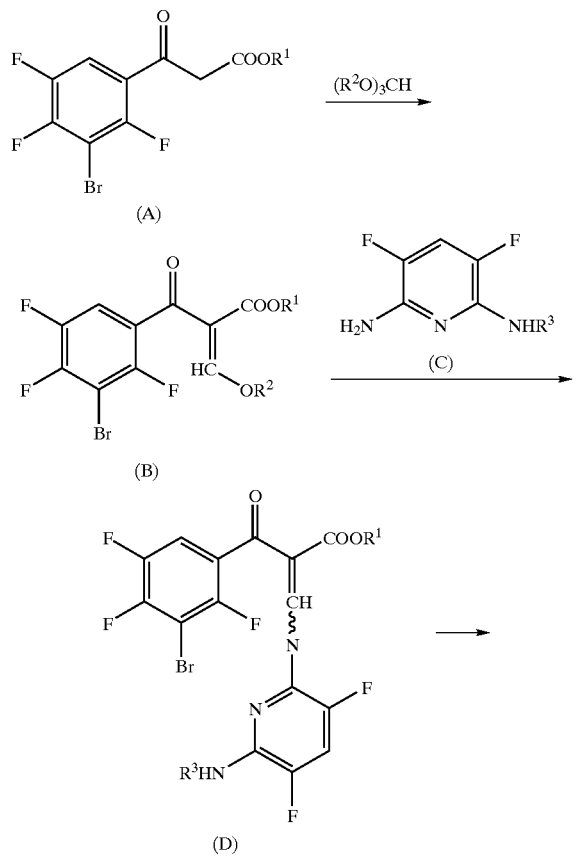

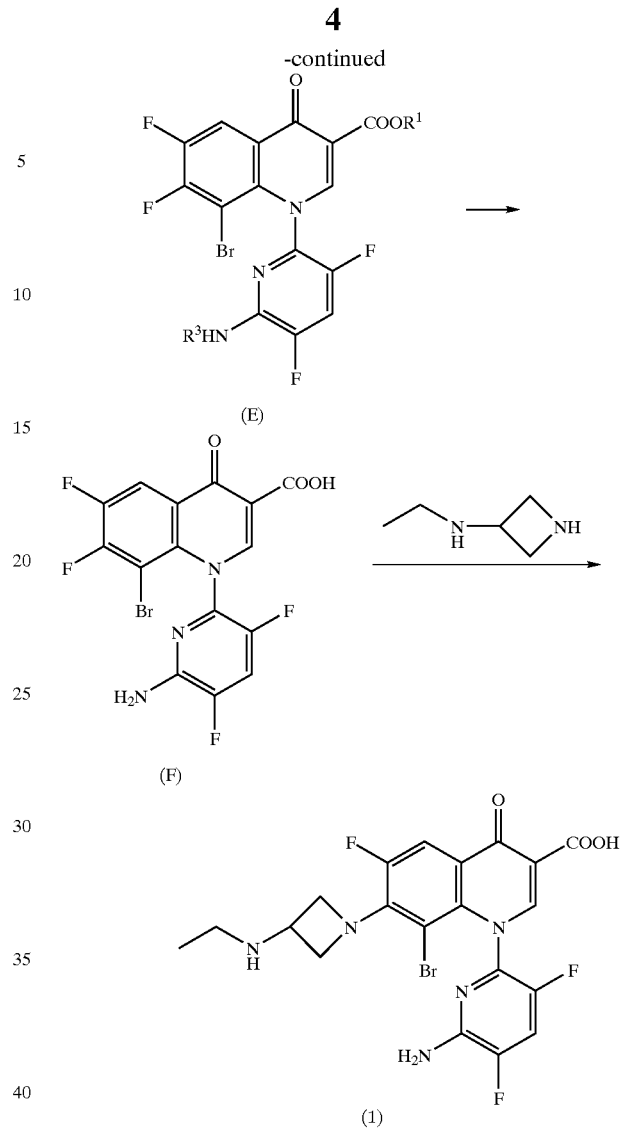

wherein R and $R^2$ represent lower alkyl groups, and $R^3$ represents a hydrogen atom or an amino-protecting group (for example, t-butyl, benzyl, p-methoxybenzyl, or 1,1,3,3-tetramethyl-butyl).

Compound 1 of the present invention can be obtained by reacting an orthoformate ester such as ethyl orthoformate or methyl orthoformate with the compound (A) to form an acrylate ester derivative (B), reacting the acrylate ester derivative with an amino compound (C) to yield a compound (D), subjecting the compound (D) to a cyclizing reaction to obtain a compound (E), hydrolyzing the compound (E) into a compound (F), and then reacting the compound (F) with 3-ethylaminoazetidine.

The reaction between the compound (A) and the orthoformate ester can be conducted generally at 0 to 160° C. preferably at 50 to 150° C., and the reaction time may be generally 10 minutes to 48 hours, preferably 1 to 10 hours. The orthoformate ester can be used preferably in an equimolar amount or greater relative to the compound (A), notably in a molar amount about 1 to 10 times as much as the compound (A). It is preferred to add, as a reaction promoter, a carboxylic acid anhydride such as acetic anhydride. This carboxylic acid anhydride can be used preferably in an equimolar amount or greater relative to the compound (A), notably in a molar amount about 1 to 10 times as much as the compound (A).

The reaction with the compound (C) is conducted in a solventless manner or in an appropriate solvent. Any solvent can be used in this reaction insofar as it does not affect the reaction. Illustrative are aromatic hydrocarbons such as benzene, toluene and xylene; ethers such as diethyl ether, tetrahydrofuran, dioxane, monoglyme and diglyme; aliphatic hydrocarbons such as pentane, hexane, heptane and ligroin; halogenated hydrocarbons such as methylene chloride, chloroform and carbon tetrachloride; aprotic polar solvents such as dimethylformamide and dimethylsulfoxide; and alcohols such as methanol, ethanol and propanol. This reaction can be conducted generally at 0 to 150° C. preferably at 0 to 100° C., and the reaction time is 10 minutes to 48 hours in general. The compound (C) can be used in an equimolar amount or greater relative to the compound (A), notably in a molar amount 1 to 2 times as much as the compound (A).

As an alternative process, an acetal such as N,N-dimethylformamide dimethylacetal or N,N-dimethylformamide diethylacetal is reacted to the compound (A), followed by a further reaction with the compound (C) to yield the compound (D). Any solvent can be used in the reaction with the acetal insofar as it does not affect the reaction. Illustrative are those exemplified above. This reaction can be conducted generally at 0 to 150° C., preferably at room temperature to 100° C., and the reaction time can range from 10 minutes to 48 hours, preferably from 1 to 10 hours.

Next, the reaction in which the compound (D) is subjected to the cyclizing reaction to obtain the compound (E) is conducted in the presence or absence of a basic compound in a solvent. Any solvent can be used in this reaction insofar as it does not affect the reaction. Illustrative are aromatic hydrocarbons such as benzene, toluene and xylene; ethers such as diethyl ether, tetrahydrofuran, dioxane, monoglyme and diglyme; halogenated hydrocarbons such as methylene chloride, chloroform and carbon tetrachloride; aprotic polar solvents such as dimethylformamide and dimethylsulfoxide; and alcohols such as methanol, ethanol and propanol. Usable as the basic compound can include, for example, alkali metals such as metallic sodium and metallic potassium; metal hydrides such as sodium hydride and calcium hydride; inorganic salts such as sodium hydroxide, potassium hydroxide, sodium carbonate and potassium carbonate; alkoxides such as sodium methoxide, sodium ethoxide and potassium t-butoxide; metal fluorides such as sodium fluoride and potassium fluoride; and organic bases such as triethylamine and 1,8-diazabicyclo[5.4.0]undecene (DBU). The temperature of the reaction ranges generally from 0 to 200° C., preferably from room temperature to 180° C., and the reaction can be completed in 5 minutes to 24 hours in general. The basic compound can be used in an equimolar amount or greater relative to the compound (D), notably in a molar amount 1 to 2 times as much as the compound (D).

Elimination of the carboxyl-protecting group as $R^1$ and the amino-protecting group as $R^3$ by hydrolysis of the compound (E) makes it possible to obtain the compound (F).

To the hydrolysis, reaction conditions employed in ordinary hydrolyses are all applicable. The hydrolysis can be effected, for example, in the presence of a basic compound such as sodium hydroxide, potassium hydroxide, sodium carbonate or potassium carbonate, a mineral acid such as hydrochloric acid, sulfuric acid or hydrobromic acid, or an organic acid such as p-toluenesulfonic acid in a solvent, for example, water, an alcohol such as methanol, ethanol or propanol, an ether such as tetrahydrofuran or dioxane, a ketone such as acetone or methyl ethyl ketone, or acetic acid, or a mixed solvent thereof. The reaction can be conducted generally at room temperature to 180° C., preferably at room temperature to 140° C., and the reaction time can generally range from 1 to 24 hours.

Further, the compound (F) is reacted to 3-ethylaminoazetidine to obtain Compound 1 of the present invention.

This reaction can be conducted in a solvent which does not affect the reaction, for example, an aromatic hydrocarbon such as benzene, toluene or xylene, an alcohol such as methanol or ethanol, an ether such as tetrahydrofuran, dioxane or monoglyme, a halogenated hydrocarbon such as methylene chloride, chloroform or carbon tetrachloride, an aprotic polar solvent such as dimethylformamide, diemthylsulfoxide or N-methylpyrrolidone, acetonitrile, or pyridine, in the presence of an acid-neutralizing agent as needed, for example sodium carbonate, calcium carbonate, triethylamine or 1,8-diazabicyclo[5.4.0]undecene (DBU), at room temperature to 160° C. The reaction time can range from several minutes to 48 hours, with a range of from 10 minutes to 24 hours being preferred. 3-Ethylaminoazetine can be used in an equimolar amount or greater relative to the compound (F), preferably in a molar amount 1 to 5 times as much as the compound (F).

Compound 1 can be converted into an acid addition salt or a base addition salt by a method known per se in the art.

This reaction can be conducted in a polar solvent, for example, an alcohol such as methanol or ethanol, or water, in the presence of a mineral acid such as hydrochloric acid, sulfuric acid or phosphoric acid, an organic carboxylic acid such as formic acid, acetic acid, citric acid, trichloroacetic acid, trifluoroacetic acid, fumaric acid or maleic acid, an organic sulfonic acid such as methanesulfonic acid, benzenesulfonic acid, p-toluenesulfonic acid, mesitylene-sulfonic acid or naphthalenesulfonic acid, a basic compound such as sodium hydroxide, potassium hydroxide, calcium hydroxide or magnesium hydroxide, or a nitrogen-containing organic base such as ammonia, trimethylamine, triethylamine, tributylamine, pyridine, N,N-dimethylaniline, N-methyl-piperidine, N-methylmorpholine, diethylamine, cyclohexyl-amine, procaine, dibenzylamine, N-benzyl-β-phenethylamine, 1-efenamine or N,N'-dibenzylethylenediamine, at room temperature or with heating as needed.

Incidentally, the starting compound (A) can be produced, for example, by the process disclosed in any one of the following publications or by a similar process.

(1) J. Heterocyclic Chem., 22, 1033 (1985)
(2) Liebigs Ann. Chem., 29 (1987)
(3) J. Med. Chem., 31, 991 (1988)
(4) J. Org. Chem., 35, 930 (1970)
(5) JP 62-246541 A
(6) JP 63-26272 A
(7) JP 63-145268 A
(8) J. Med. Chem., 29, 2363 (1986)
(9) J. Fluorin. Chem. 28, 361 (1985)
(10) JP 63-198664 A
(11) JP 63-264461 A
(12) JP 63-104974 A On the other hand, the reactant compound (C) can be produced by a desired process. For example, it can be produced by substituting an amine derivative for a halogen atom bonded to a carbon atom, which is a constituent of a 6-membered ring, in accordance with a known halogen-amine substitution reaction such as that disclosed in WO 97/11068 A or WO 97/38971 A.

The compound of the present invention obtained as described above can be isolated and purified in a manner known per se in the art. Depending on the conditions for isolation and purification, it is obtained in the form of a salt or in the form of a free carboxylic acid or a free amine. These two forms can be converted from one to the other as desired, and the compound of the present invention can be produced in an intended form.

Compound 1, which has a 6-amino-3,5-difluoropyridinyl group at the 1-position, an ethylaminoazetidinyl group at the 7-position and a bromine atom at the 8-position, and its salts obtained as described above, as will be demonstrated in Tests 1–4, have effects unpredictable from the structure-activity correlations accepted to date in connection with the pyridonecarboxylic acid derivatives represented by the formula (I), that is, have a long blood half-life when administered orally, and show an extremely high value of 78% in terms of bioavailability as calculated from an AUC up to $24^{th}$ hour after administration while retaining excellent properties such as extremely good antimicrobial potency and non-exhibition of phototoxicity which is toxicity specific to quinolone. Further, Compound 1 an its salts also have excellent properties that they are lower in antihypertensive effect and side effects to skin, such as eruption, than known compounds of similar structures.

Compound 1 and its salts according to the present invention can each be formulated as an antimicrobial agent together with pharmaceutically acceptable carriers into compositions for parenteral administration such as injection, rectal administration or installation or oral administration in solid or liquid forms.

Exemplary preparations for injection can include pharmaceutically acceptable, sterile, aqueous or non-aqueous solutions, suspensions and emulsions. Illustrative or non-aqueous carriers, diluents, solvents and vehicles are propylene glycol, polyethylene glycol, vegetable oils, for example, olive oil, and injectable organic esters, for example, ethyl oleate. Such solutions can also contain additives such as preservatives, moistening agents, emulsifiers and dispersants as needed. These injections can be sterilized, for example, by filtration them through bacterial filters or by adding, immediately before use, sterilizing agents as are or in the form of sterile solid compositions soluble in some other sterile media for injection.

To preparations for instillatory administration, solubilizers, preservatives, isotonicities, thickeners and the like can be added as needed in addition to the compounds according to the present invention.

Exemplary solid preparations for oral administration can include capsules, tablets, pills, powders and granules. Upon formulation of such solid preparations, the compounds according to the present invention are generally mixed with at least one inert extender, for example, sucrose, lactose or starch. In the formulation of ordinary preparations, materials other than inert extenders, such as lubricants (for example, magnesium stearate), may also be used. In capsules, tablets and pills, buffers may be used. To tablets and pills, enteric coatings may be applied.

Exemplary liquid preparations for oral administration can include pharmaceutically acceptable emulsions, solutions, suspensions, syrups and elixirs, contain commonly-employed inert diluents, for example, water. In addition to such inert diluents, additives such as wetting agents, emulsifying or suspending agents, sweeteners, seasonings and flavors may also be added.

Preparations for rectal administration can contain, in addition to the compounds according to the present invention, excipients such as cacao butter and suppository wax.

The dosage of each compound of the present invention varies depending upon the properties of the compound, the administration route, the desired treatment period and other factors. In general, however, its daily dosage may preferably range from about 0.1 to 1,000 mg/kg, with a range of from about 0.5 to 100 mg/kg being particularly preferred. Further, this daily dosage can be administered in 2 to 4 portions as desired.

EXAMPLES

The present invention will hereinafter be described in further detail by Examples and Referential Examples.
Referential Example 1

Synthesis of ethyl 8-bromo-1-[6-(t-butylamino)-3,5-difluoropyridin-2-yl]-6,7-difluoro-4-oxo-1,4-dihydroquinoline-3-carboxylate To a chloroform solution (5 mL) in which ethyl 3-ethoxy-2-(3-bromo-2,4,5-trifluorobenzoyl)acrylate prepared from ethyl 3-bromo-2,4,5-trifluorobenzoylacetate (1.32 g) in a manner known per se in the art was dissolved, 2-amino-6-(t-butylamino) -3,5-difluoropyridine was added under TLC monitoring of the reaction until conversion into an amino acrylate derivative was completed. The reaction mixture was concentrated under reduced pressure to obtain a yellow solid residue. To the residue, anhydrous potassium carbonate (1.2 g) and N,N-dimethylformamide (2 mL) were added, and the mixture was stirred at 90° for 15 minutes. The mixture was allowed to cool down. Chloroform (30 mL) and distilled water (300 mL) were added, and the mixture was allowed to separate into layers. The chloroform layer was washed twice with distilled water (300 mL), dried over anhydrous magnesium sulfate, concentrated under reduced pressure, and then left over. The precipitate was collected by filtration, and washed successively with ethanol and diisopropyl ether in this order to obtain the title compound (1.41 g) as a colorless powder.

Melting point: 198–203° C.
$^{1}$H-NMR(CDCl$_{3}$)δ: 1.38(s, 9H), 1.40(t, J=7 Hz, 3H), 4.04(q, J=7 Hz, 2H), 4.71(brs, 1H), 7.20(dd, J=8 Hz, 10 Hz, 1H), 8.36(dd, J=9 Hz, 10 Hz, 1H), 8.54(s, 1H).
Referential Example 2

Synthesis of 1-(6-amino-3,5-difluoropyridin-2-yl)-8-bromo-6,7-difluoro-4-oxo-1,4-dihydroquinoline-3-carboxylic acid Ethyl 8-bromo-1-[6-(t-butylamino)-3,5-difluoro-pyridin-2-yl]-6,7-difluoro-4-oxo-1,4-dihydroquinoline-3-carboxylate (1.38 g) was added to a liquid mixture of 12% hydrochloric acid (3.5 mL) and acetic acid (3.5 mL), and the mixture was heated for 5 hours under stirring and reflux. Subsequent to addition of distilled water (5 mL), the mixture was allowed to cool down. The precipitate was collected by filtration, and washed successively with ethanol and diisopropyl ether in this order to obtain the title compound (1.10 g) as a colorless powder.

Melting point: 272–278° C.
$^{1}$H-NMR (D$_{6}$-DMSO)δ: 6.80(s, 2H), 7.99(t, J=9 Hz, 1H), 8.38(t, J=9 Hz, 1H), 8.93(s, 1H).

Example 1

Synthesis of 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid (Compound 1)

3-Ethylaminoazetidine (700 mg), 1-(6-amino-3,5-difluoropyridin-2-yl)-8-bromo-6,7-difluoro-4-oxo-1,4-dihydroquinoline-3-carboxylic acid (1.5 g), N-methyl-pyrrolidine (2.0 g)and dimethylsulfoxide (4.5 g) were combined, and the mixture was heated under stirring at 40° C. for 24 hours. After the mixture was allowed to cool down, isopropyl ether (10 mL) was added, the mixture was stirred, and a clear layer at the top of the mixture was removed. The same procedure was repeated once more, and the residue was concentrated under reduced pressure. Ethanol (5 mL) was added, and the mixture was heated under stirring at 70° C. for 30 minutes. The precipitated solid was collected by filtration. The title compound (1.38 g) was obtained.

Appearance: Colorless powder

Melting point: 195–196° C.

$^1$H-NMR (D$_6$-DMSO)δ: 0.99(t, J=7 Hz, 3H), 2.48(q, J=7 Hz, 2H), 4.05–4.15(m, 2H), 4.35–4.42(m, 1H), 4.60–4.69 (m, 2H), 6.74(brs, 2H), 7.88(d, J=14 Hz, 1H), 7.93(t, J=9 Hz, 1H), 8.69(s, 1H).

Example 2

Synthesis of 1-(6-amino-3,5-difluoropyridin-2-yl)-8-bromo-7-(3-ethylaminoazetidin-1-yl)-6-fluoro-4-oxo-1,4-dihydroquino line-3-carboxylic acid maleate (Compound 2)

1-(6-Amino-3,5-difluoropyridin-1-yl)-6-fluoro-4-oxo-1,4-dihydroquinoline-3-carboxylic acid (1.38 g) was added to ethanol (13 mL), and to the mixture, maleic acid (400 mg) was added gradually. The mixture was heated under stirring at 70° C. for 5 hours. After the mixture was allowed to cool down, a solid was collected by filtration. The solid was washed with ethanol.

The title compound (1.33 g) was obtained.

Appearance: Colorless powder

Melting point: 196–199° C.

$^1$H-NMR(D$_6$-DMSO)δ: 1.16(t, J=7 Hz, 3H), 2.93(q, J=7 Hz, 2H), 3.99–4.06(m, 1H), 4.41–4.48(m, 1H), 4.50–4.56 (m, 1H), 4.67–4.74(m, 1H), 4.74–4.82(m, 1H), 6.02(s, 2H), 6.76(brs, 2H), 7.95(t, J=9 Hz, 1H), 7.97(d, J=14 Hz, 1H), 8.75(s, 1H).

Tests

The results of tests on the compound of the present invention for antimicrobial effects, phototoxicity and in vivo distribution will be described in Tests 1–4. As comparative compounds, the following compounds disclosed in WO 97/11068 A and commercially-available ciprofloxacin (CPFX) and levofloxacin (LVFX) were used.

Comparative Compound 1: 1-(6-amino-3,5-difluoropyridin-2-yl)-8-bromo-7-(3-methylaminoazetidin-1-yl)-6-fluoro-4-oxo-1,4-dihydroquinoline-3-carboxylic acid.

Comparative Compound 2: 1-(6-amino-3,5-difluoropyridin-2-yl)-8-chloro-7-(3-ethylaminoazetidin-1-yl)-6-fluoro-4-oxo-1,4-dihydroquinoline-3-carboxylic acid.

CPFX: 1-cyclopropyl-6-fluoro-7-(1-piperadinyl)-1,4-dihydro-4-oxoquinoline-3-carboxylic acid.

LVFX: S(−)-9-fluoro-2,3-dihydro-3-methyl-10-(4-methyl-1-piperazinyl)-7-oxo-7H-pyrido[1,2,3-de][1,4]benzoxazine-6-carboxylic acid.

(1) Antimicrobial Effects

Their minimum growth inhibitory concentrations (MICs: μg/mL) were determined in accordance with the standard method of the Japan Society of Chemotherapy [Chemotherapy, 29(1), 76 (1981)]. The results are presented in Table 1.

TABLE 1

|  | Comp'd 1 | Comp. Comp'd 1 | Comp. Comp'd 2 | CPFX | LVFX |
| --- | --- | --- | --- | --- | --- |
| S. aureus 209P | 0.013 | 0.013 | 0.013 | 0.2 | 0.2 |
| MRSA W200 | 0.013 | 0.025 | 0.025 | 0.78 | 0.39 |
| S. epidermidis IFO12293 | 0.025 | 0.05 | 0.05 | 1.56 | 0.78 |
| E. faecalis IFO12580 | 0.39 | 0.39 | 0.78 | 1.56 | 1.56 |
| M. luteus IFO12708 | 0.39 | 0.39 | 0.78 | 3.13 | 0.78 |
| B. subtilis ATCC6633 | 0.025 | 0.05 | 0.025 | 0.05 | 0.1 |
| E. coli NIHJ-JC2 | 0.025 | 0.013 | 0.025 | 0.025 | 0.05 |
| K. pneumoniae KC-1 | 0.05 | 0.025 | 0.05 | 0.05 | 0.1 |
| P. vulgaris IFO3167 | 0.1 | 0.1 | 0.2 | 0.05 | 0.05 |
| S. marcescens IFO3736 | 1.56 | 1.56 | 1.56 | 0.2 | 0.78 |
| P. aeruginosa IFO3445 | 0.78 | 0.39 | 0.39 | 0.39 | 0.78 |
| P. aeruginosa E-2 | 1.56 | 0.78 | 1.56 | 0.78 | 1.56 |

(2) Phototoxicity Test

A phototoxicity test was performed by the following procedure.

Female ICR mice (5 to 6 weeks old) were intravenously administered with the test compounds (40 mg/kg/10 mL), respectively, and were exposed for 4 hours to ultraviolet rays (320 to 400 nm, 1.8 mW/cm$^2$/sec). Their ears were observed for abnormality at 0 hour (immediately after the exposure) and after 24 and 48 hours.

Ear abnormality was ranked by the following standards: no abnormality (0 point), mild erythema (1 point), medium erythema (2 points), and severe erythema or edema (3 points) The results are presented in Table 2.

TABLE 2

|  | 0 hour (point, frequency) | 24 hours | 48 hours |
| --- | --- | --- | --- |
| Compound 1 | 0, 0/3 | 0, 0/3 | 0, 0/3 |
| Comp. Comp'd 1 | 0, 0/3 | 0, 0/3 | 0, 0/3 |
| Comp. Comp'd 2 | 0.7, 2/3 | 0, 0/3 | 0, 0/3 |

(3) Antibacterial Effects on Clinically-isolated Quinolone Resistant Pneumococci Using agar plates added with 5% defibrinated sheep blood, minimum growth inhibition concentrations (MICs; μg/mL) against certain pneumococci were determined in accordance with the standard method of the Japan Society of Chemotherapy [Chemotherapy, 29(1), 76 (1981)]. The results are presented in Table 3.

TABLE 3

|  | Compound 1 | Comp. Comp'd 1 | CPFX | LVFX |
| --- | --- | --- | --- | --- |
| Isolated coccus 1 | 0.03 | 0.06 | 8 | 2 |
| Isolated coccus 5 | 0.12 | 0.5 | 64 | 32 |

From the results of Table 1 to Table 3, the compound according to the present invention exhibited antimicrobial activities comparable with or better than the comparative compounds, and was also negative in phototoxicity.

(4) In vivo Pharmacokinetic Study

An investigation was made on the absorption and excretion of the compounds of the present invention in and from dogs.

A 0.5% suspension of one of the test compounds in methyl cellulose (10 mg/mL/kg) was forcedly administered per os to 2–4 years old, male beagles fasted for 16 to 17 hours. After the administration, blood samples were collected on the $0.25^{th}$, $0.5^{th}$, $1^{st}$, $2^{nd}$, $4^{th}$, $6^{th}$, $8^{th}$ and $24^{th}$ hours, and serum samples were obtained. To determine urinary excretion rates, urine samples were also collected up to $24^{th}$ hour after the administration. The concentrations of the test compound in the serum samples and urine samples were measured by the paper disk method making use of *Bacillus subtilis* ATCC6633 as a test bacterium, and the absorption and excretion were ranked. The results so obtained are presented in Table 4.

TABLE 4

| | N | $C_{max}$ (μg/mL) | $T_{max}$ (hr) | $T_{1/2}$ (hr) | AUC 0–8 hr (μg · hr/mL) | Urinary excretion rate (%) |
|---|---|---|---|---|---|---|
| Compound 1 | 3 | 4.82 | 1 | 3.8 | 22.8 | 19.8 |
| Compound 2 | 3 | 3.73 | 1 | 4.8 | 17.6 | 17.4 |
| Comparative Compound 1 | 2 | 2.35 | 0.5 | 2.0 | 8.54 | 14.8 |
| The maleate salt of Comparative Compound 1 | 3 | 1.49 | 1 | 3.8 | 7.66 | 16.7 |

It has been confirmed from Table 4 that the compounds of the present invention have in vivo pharmacokinetic study significantly improved over the comparative compounds.

INDUSTRIAL APPLICABILITY

Compound 1 and its salts according to the present invention have characteristic properties that, when administered orally, they exhibit long blood half-time and extremely high bioavailability while retaining the properties that they are extremely high in antimicrobial effects and low in toxicity. Compound 1 and its salts also have excellent properties that they are lower in antihypertensive effect and side effects to skin, such as eruption, than known compounds of similar structures. Compound 1 and its salts, therefore, can be used widely as preventives and therapeutics for various infectious diseases of human and animals and also as fish drugs, agrichemicals, food preservatives and the like. Further, Compound 1 of the present invention is expected to have antiviral effects, especially anti-HIV (human immunodeficiency virus) effects, and is considered to be effective for the prevention or treatment of AIDS.

What is claimed is:

1. 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid or a salt thereof.

2. A medicinal composition comprising an effective amount of 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid or a salt thereof and a pharmaceutically acceptable carrier.

3. A method for the treatment of a microbial infection which comprises administering an effective amount of 1-(6-amino-3,5-difluoropyridin-2-yl)-8-bromo-7-(3-ethylaminoazetidin-1-yl)-6-fluoro-4-oxo-1,4-dihydroquinoline-3-carboxylic acid or a salt thereof to a patient in need thereof.

4. The compound according to claim 1, wherein said compound is an acid addition salt in a base addition salt.

5. The compound according to claim 1, wherein said compound is an acid addition salt.

6. The compound according to claim 1, wherein said compound is an acid addition salt selected from the group consisting of maleate, methane-sulfonate, p-toluene sulfonate and hydrochloride.

7. The method according to claim 3, wherein the daily dosage is from about 0.1 to 1000 mg/kg.

8. The method according to claim 3, wherein the daily dosage is from about 0.5 to 100 mg/kg.

9. The method according to claim 3, wherein the microbial infection is a bacterial infection.

10. The method according to claim 9, wherein the bacterial infection is a pneumococci infection.

* * * * *